US010799148B2

(12) United States Patent
Mosesov et al.

(10) Patent No.: US 10,799,148 B2
(45) Date of Patent: *Oct. 13, 2020

(54) SYSTEM AND METHOD FOR DETECTING SHEATHING AND UNSHEATHING OF LOCALIZATION ELEMENTS

(71) Applicant: St. Jude Medical, Cardiology Division, Inc., St. Paul, MN (US)

(72) Inventors: Artem Mosesov, Roseville, MN (US); Anthony D. Hill, Minneapolis, MN (US); Birin Yucesan, Woodbury, MN (US); Timothy G. Curran, Ramsey, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 73 days.

This patent is subject to a terminal disclaimer.

(21) Appl. No.: 16/223,415

(22) Filed: Dec. 18, 2018

(65) Prior Publication Data
US 2019/0167150 A1 Jun. 6, 2019

Related U.S. Application Data

(63) Continuation of application No. 15/148,298, filed on May 6, 2016, now Pat. No. 10,188,314.

(Continued)

(51) Int. Cl.
*A61B 5/06* (2006.01)
*A61B 5/00* (2006.01)
(Continued)

(52) U.S. Cl.
CPC ............ *A61B 5/063* (2013.01); *A61B 5/0422* (2013.01); *A61B 5/064* (2013.01); *A61B 5/6852* (2013.01);
(Continued)

(58) Field of Classification Search
CPC ................................. A61B 5/063; A61B 5/20
(Continued)

(56) References Cited

U.S. PATENT DOCUMENTS

| 5,697,377 A | 12/1997 | Wittkampf |
| 5,983,126 A | 11/1999 | Wittkampf |

(Continued)

FOREIGN PATENT DOCUMENTS

| JP | 2006-122324 | 5/2006 |
| WO | 2008/082802 | 7/2008 |

OTHER PUBLICATIONS

International Search Report and Written Opinion for PCT Application No. PCT/US2014/019891, dated May 23, 2014.
(Continued)

*Primary Examiner* — Nadia A Mahmood
(74) *Attorney, Agent, or Firm* — Wiley Rein LLP

(57) ABSTRACT

A method of detecting a localization element/sheath state change with a localization system includes establishing a localization field using a plurality of localization field generators, obtaining first and second localization signals from first and second catheter-borne localization elements within the localization field, respectively, comparing the quadrature components of the first and second localization signals, and detecting a localization element/sheath state change for one of the catheter-borne localization elements based on the comparison between quadrature components. For example, withdrawal of a localization element into an introducer sheath can be detected when the comparison between quadrature components exceeds a preset amount. Conversely, re-emergence of the localization element from the introducer sheath can be detected when the comparison between quadrature components returns below the preset amount.

13 Claims, 7 Drawing Sheets

Related U.S. Application Data

(60) Provisional application No. 62/158,238, filed on May 7, 2015.

(51) Int. Cl.
  *A61B 5/042* (2006.01)
  *A61B 34/20* (2016.01)
  *A61B 90/00* (2016.01)

(52) U.S. Cl.
  CPC .............. *A61B 34/20* (2016.02); *A61B 90/39* (2016.02); *A61B 5/042* (2013.01); *A61B 5/6885* (2013.01); *A61B 2034/2051* (2016.02); *A61B 2560/0223* (2013.01); *A61B 2560/0266* (2013.01)

(58) Field of Classification Search
  USPC ........................................................ 600/508
  See application file for complete search history.

(56) References Cited

U.S. PATENT DOCUMENTS

| | | |
|---|---|---|
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,885,707 B2 | 2/2011 | Hauck |
| 9,026,196 B2 | 5/2015 | Curran et al. |
| 2004/0254437 A1 | 12/2004 | Hauck |
| 2007/0213616 A1 | 9/2007 | Anderson et al. |
| 2008/0255470 A1 | 10/2008 | Hauck et al. |
| 2009/0262109 A1 | 10/2009 | Markowitz et al. |
| 2013/0303886 A1 | 11/2013 | Ludwin et al. |
| 2014/0257071 A1 | 9/2014 | Curran et al. |

OTHER PUBLICATIONS

International Search Report for PCT Application No. PCT/US2016/031106, dated Jul. 21, 2016.

SYSTEM AND METHOD FOR DETECTING SHEATHING AND UNSHEATHING OF LOCALIZATION ELEMENTS

CROSS-REFERENCE TO RELATED APPLICATIONS

This application is a continuation of U.S. application Ser. No. 15/148,298, filed 6 May 2016 ("the '298 application"), now U.S. Pat. No. 10,188,314, which claims the benefit of U.S. provisional application No. 62/158,238, filed 7 May 2015 ("the '238 application"). This application is also related to U.S. application Ser. No. 13/785,807, filed 5 Mar. 2013 ("the '807 application"), now U.S. Pat. No. 9,026,196. The '298, '238, and '807 applications are hereby incorporated by reference as though fully set forth herein.

BACKGROUND

The instant disclosure relates to localization systems, such as those used in cardiac diagnostic and therapeutic procedures. In particular, the instant disclosure relates to systems, apparatuses and methods for detecting when a localization element(s), such as an electrode(s), emerges from and/or is retracted into an introducer sheath or other enveloping instrument.

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. In many instances, the catheters are inserted into the body and navigated to the target location with the aid of an introducer sheath (sometimes referred to as simply an "introducer" or a "sheath"). As the ordinarily skilled artisan will appreciate, an introducer is a catheter with a central lumen through which other medical devices can be passed.

It is also known to track the three-dimensional coordinates of a catheter or other medical device moving within a patient's body using a localization system (sometimes also referred to as a "mapping system," "navigation system," or "positional feedback system"). These devices typically use magnetic, electrical, ultrasound, and other radiation sources to determine the coordinates of these devices. For example, impedance-based localization systems determine the coordinates of the medical device by interpreting a voltage measured by the medical device (more particularly, the voltages measured by one or more electrodes carried on the medical device) as a location within an electrical field.

One drawback of an impedance-based system, however, is that impedance-based localizations can become distorted when the medical device is withdrawn into the introducer. This is because the introducer is normally made of an insulating material, such that the voltage gradient in the vicinity of localization electrodes within the sheath becomes non-linear and erratic. Indeed, a localization electrode within a sheath may appear to wander widely, making it difficult for the localization system to accurately and precisely render an image of the medical device for the practitioner.

BRIEF SUMMARY

Disclosed herein is a method of detecting a localization element/sheath state change with a localization system including: establishing a localization field using a plurality of localization field generators; obtaining a first localization signal from a first catheter-borne localization element positioned within the localization field via an introducer sheath, the first localization signal including a first in-phase component and a first quadrature component; obtaining a second localization signal from a second catheter-borne localization element positioned within the localization field via the introducer sheath, the second localization signal including a second in-phase component and a second quadrature component; comparing the second quadrature component to the first quadrature component; and detecting a localization element/sheath state change for the second catheter-borne localization element based on the comparison between the second quadrature component and the first quadrature component. The catheter-borne localization element can be adjacent to the second catheter-borne localization element. For example, the first catheter-borne localization element can be a tip electrode, and the second catheter-borne localization element can be a distal-most ring electrode that is proximally adjacent the tip electrode.

Withdrawal of the second catheter-borne localization element into the introducer sheath can be detected when the comparison between the second quadrature component and the first quadrature component exceeds a preset amount. Conversely, re-emergence of the second catheter-borne localization element from the introducer sheath can be detected when the comparison between the second quadrature component and the first quadrature component returns below the preset amount.

Additional comparisons are also contemplated. Thus, in some embodiments, the method can also include: obtaining a third localization signal from a third catheter-borne localization element positioned within the localization field via the introducer sheath, the third localization signal including a third in-phase component and a third quadrature component; comparing the second quadrature component to the third quadrature component; and detecting a localization element/sheath state change for the second catheter-borne localization element based on the comparison between the second quadrature component and the first quadrature component and the comparison between the second quadrature component and the third quadrature component. Further, withdrawal of the second catheter-borne localization element into the introducer sheath can be detected when the comparison between the second quadrature component and the first quadrature component exceeds a first preset amount and the comparison between the second quadrature component and the third quadrature component exceeds a second preset amount.

In embodiments where the first catheter-borne localization element is a tip electrode and the second catheter-borne electrode is a proximally adjacent ring electrode, the method can also include: establishing a baseline quadrature component for the tip electrode with the tip electrode outside the introducer sheath; and detecting a localization element/sheath state change for the tip electrode when the first quadrature component deviates from the baseline quadrature component by more than a preset amount. The baseline quadrature component for the tip electrode can be established upon detecting that the ring electrode has been withdrawn into the introducer sheath. Alternatively, the baseline quadrature component for the tip electrode can be established when the ring electrode is outside of the introducer sheath. For example, the baseline quadrature component for the tip electrode can be computed as a running average of the first quadrature component when the ring electrode is outside of the introducer sheath.

To account for the non-homogenous structure of the cardiac space, a plurality of baseline quadrature components can be established for the tip electrode, with each baseline quadrature component corresponding to a respective anatomical region.

In still other embodiments, a state of the tip electrode is set to in-sheath upon detecting that the ring electrode has withdrawn into the introducer sheath based on the comparison between the second quadrature component and the first quadrature component. Similarly, the state of any catheter-borne localization element positioned proximally of the second catheter-borne localization element can be set to in-sheath upon detecting that the second catheter-borne localization element has withdrawn into the introducer sheath based on the comparison between the second quadrature component and the first quadrature component.

Also disclosed herein is a method of conducting a cardiac electrophysiology study, including: establishing an impedance-based localization field encompassing a patient's body; obtaining a localization signal from a first localization element on a medical device positioned within the patient's body via an introducer sheath, the first localization signal including a first in-phase component reflecting a position of the first localization element within the localization field and a first quadrature component; obtaining a localization signal from a second localization element on the medical device, the second localization signal including a second in-phase component reflecting a position of the second localization element within the localization field and a second quadrature component; comparing the second quadrature component to the first quadrature component; and detecting whether the second localization element is within or outside of the introducer sheath based upon the comparison of the second quadrature component to the first quadrature component.

Detecting whether the second localization element is within or outside of the introducer sheath based upon the comparison of the second quadrature component to the first quadrature component can include detecting that the second localization element is within the introducer sheath when the comparison exceeds a preset amount. Data collection can be suspended when the second localization element is detected within the introducer sheath. Alternatively, data collected by the second localization element when the second localization element is detected within the introducer sheath can be discarded. In addition, a state of the first localization element can be set to within the introducer sheath when the second localization element is detected within the introducer sheath.

The method can also include: establishing a baseline quadrature component for the first localization element with the first localization element positioned outside of the introducer sheath; and when the second localization element is detected within the introducer sheath: comparing the first quadrature component to the baseline quadrature component; and detecting whether the first localization element is within or outside of the introducer sheath based upon the comparison of the first quadrature component to the baseline quadrature component. The baseline quadrature component can be specific to an anatomical region of interest.

The instant disclosure also includes a localization system having: a localization processor configured to receive as input a first localization signal from a first localization element and a second localization signal from a second localization element; to resolve the first localization signal into a first in-phase component reflective of a position of the first localization element within a localization field and a first quadrature component; and to resolve the second localization signal into a second in-phase component reflective of a position of the second localization element within the localization field and a second quadrature component; and a state detection processor configured to receive as input the first quadrature component and the second quadrature component; and to detect whether the second localization element is within or outside of an introducer sheath by comparing the second quadrature component to the first quadrature component.

The state detection processor can further be configured to set a state of the first localization element to within the introducer sheath upon detecting that the second localization element is within the introducer sheath.

The state detection processor can further be configured to determine a baseline quadrature component for the first localization element with the first localization element outside of the introducer sheath; and to detect whether the first localization element is within or outside of the introducer sheath by comparing the first quadrature component to the baseline quadrature component.

The foregoing and other aspects, features, details, utilities, and advantages of the present invention will be apparent from reading the following description and claims, and from reviewing the accompanying drawings.

DETAILED DESCRIPTION

The instant disclosure provides methods, apparatuses and systems for detecting when a localization element, such as a localization electrode, emerges from and/or is withdrawn into another device such as an introducer sheath (referred to herein as a "localization element/sheath state change"). For purposes of illustration, embodiments hereof will be described in detail herein in the context of a localization system utilized in a cardiac electrophysiology procedure. It is contemplated, however, that the teachings herein may be applied to good advantage in other contexts.

Figure 1:
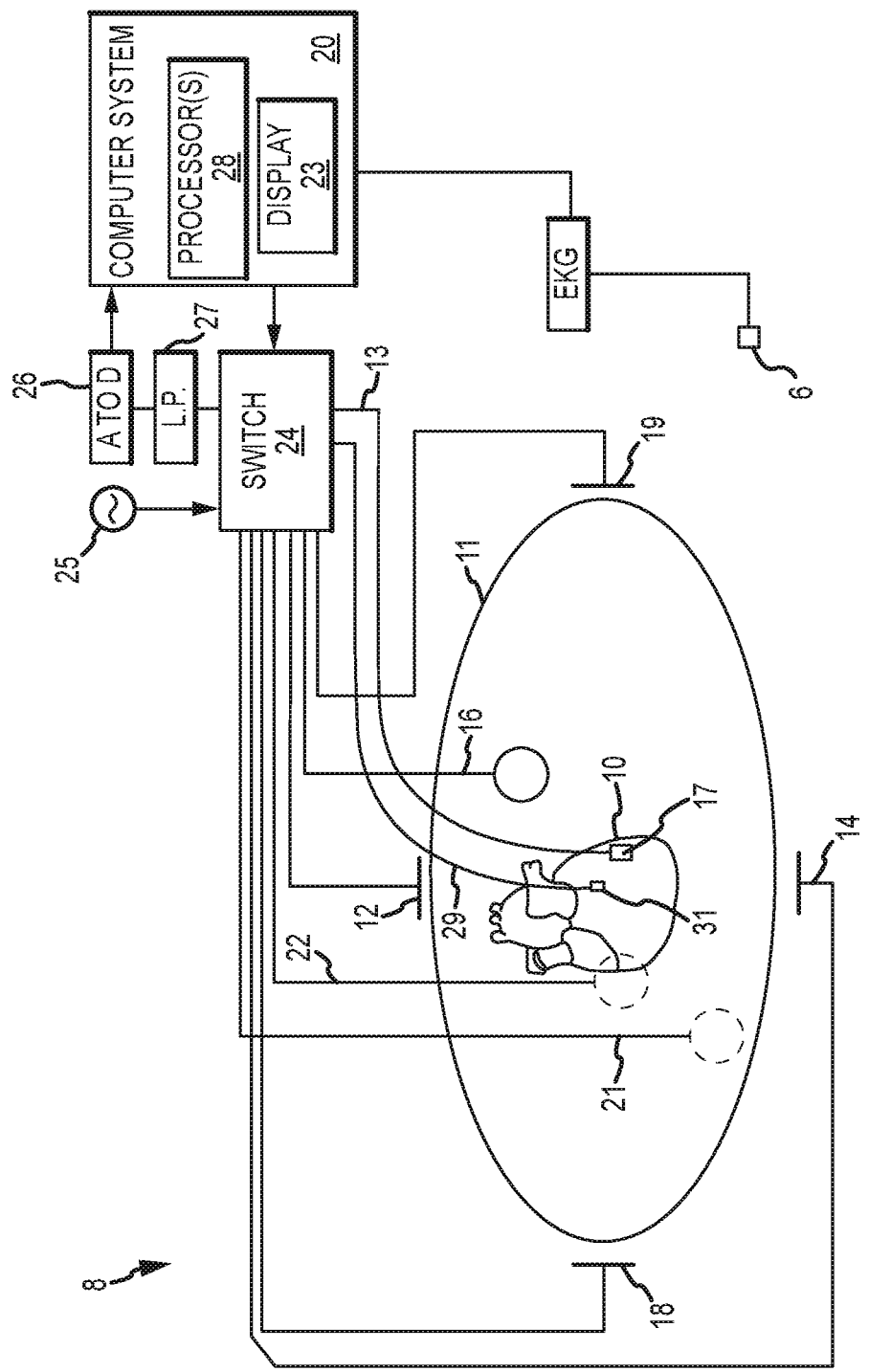
FIG. 1 is a schematic diagram of a localization system, such as may be used in an electrophysiology study.

FIG. 1 shows a schematic diagram of an electrophysiology system 8 for conducting cardiac electrophysiology studies by navigating a cardiac catheter and measuring electrical activity occurring in a heart 10 of a patient 11 and three-dimensionally mapping the electrical activity and/or information related to or representative of the measured electrical activity. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 can determine the location, and in some aspects the orientation, of objects, typically within a three-dimensional space, and express those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, such as, for example multiple electrodes on a particular body surface. As a further alternative, the electrodes do not need to be on the body surface, but could be positioned internally to the body or on an external frame.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along the sternum and spine of the patient in the thorax region, and may be referred to as the Chest and Back electrodes. The z-axis electrodes 16, 22 are applied along a third axis generally orthogonal to both the x-axis and the y-axis, such as along the inner thigh and neck regions of the patient, and may be referred to as the Left Leg and Neck electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional surface electrocardiogram ("ECG" or "EKG") system leads in place. In certain embodiments, for example, a standard set of 12 ECG leads may be utilized for sensing electrocardiograms of the patient's heart 10. This ECG information is available to the system 8 (e.g., it can be provided as input to computer system 20). Insofar as ECG leads are well understood, and for the sake of clarity in the figures, only one lead 6 and its connection to computer system 20 is illustrated in FIG. 1.

A representative catheter 13 having at least one electrode 17 (e.g., a distal electrode) is also depicted in schematic fashion. This representative catheter electrode 17 can be referred to as a "measurement electrode." Typically, multiple electrodes on catheter 13, or on multiple such catheters, will be used. In one embodiment, for example, system 8 may utilize sixty-four electrodes on twelve catheters disposed within the heart and/or vasculature of the patient. In other embodiments, system 8 may utilize a single catheter that includes multiple (e.g., eight) splines, each of which in turn includes multiple (e.g., eight) electrodes. Of course, these embodiments are merely exemplary, and any number of electrodes and catheters may be used. Indeed, in some embodiments, a high density mapping catheter, such as the EnSite™ Array™ non-contact mapping catheter of St. Jude Medical, Inc., can be utilized.

Figure 2:
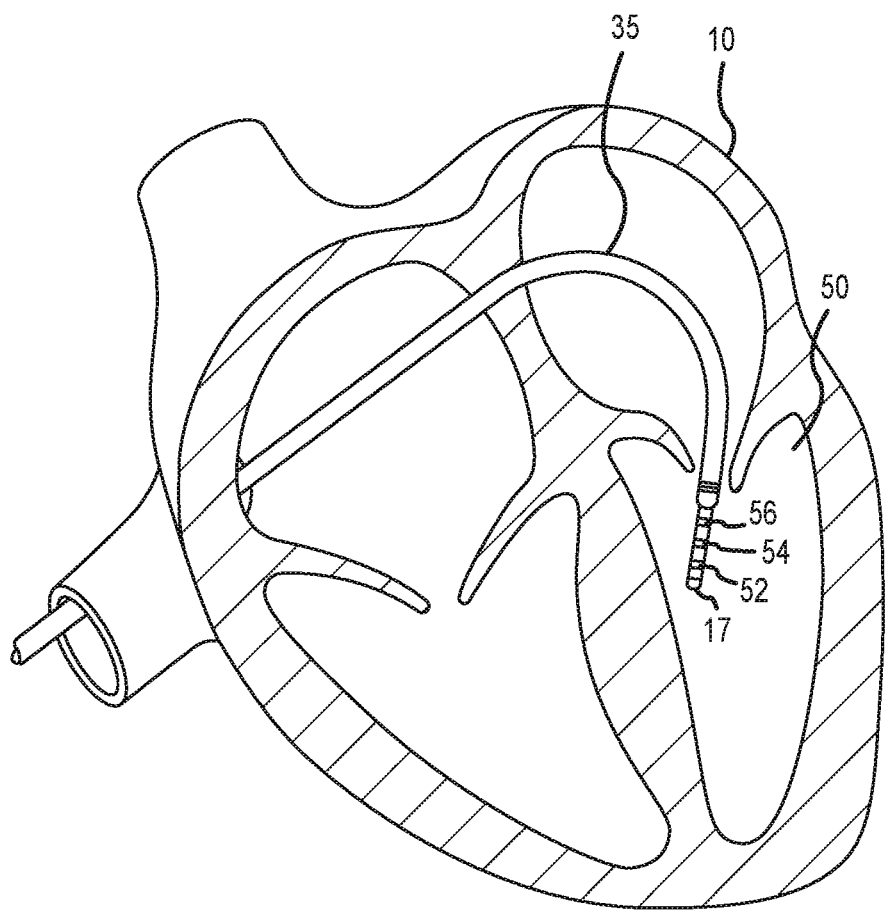
FIG. 2 depicts an exemplary catheter used in an electrophysiology study.

Likewise, it should be understood that catheter 13 (or multiple such catheters) are typically introduced into the heart and/or vasculature of the patient via one or more introducers and using familiar procedures. For purposes of this disclosure, a segment of an exemplary catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart 10 in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Figure 3A:
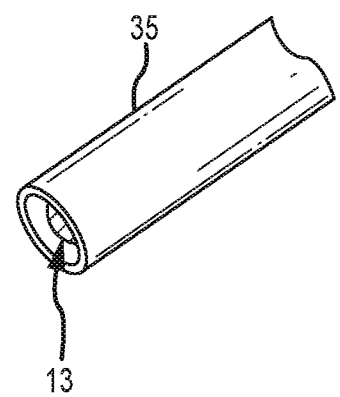
FIGS. 3A through 3C are exemplary perspective views of relative positions of localization electrodes and an introducer sheath.
Figure 3B:
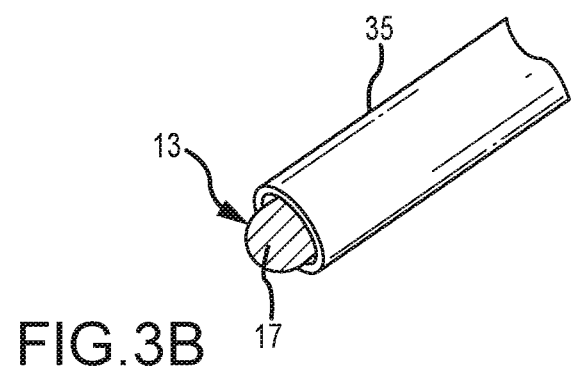
Figure 3C:
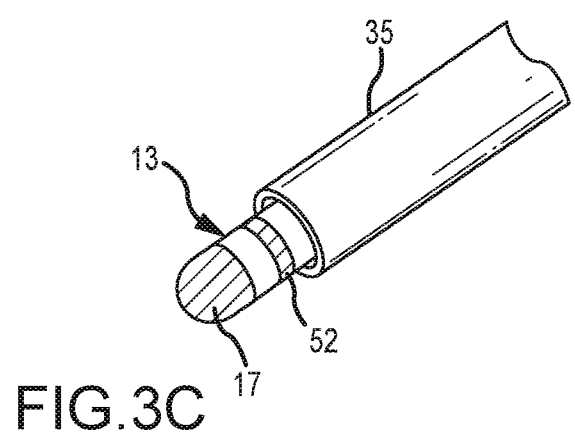

FIGS. 3A through 3C illustrate three relative positions of the distal end of catheter 13 relative to introducer 35. As shown in FIG. 3A, catheter 13 is fully withdrawn into sheath 35 (e.g., electrodes 17, 52, 54, and 56 are all within sheath 35). In FIG. 3B, catheter 13 has been advanced such that electrode 17, but not electrodes 52, 54, and 56, have emerged from sheath 35. In FIG. 3C, catheter 13 has been advanced further, such that electrodes 17 and 52, but not electrodes 54 and 56, have emerged from sheath 35. As discussed in further detail below, the teachings herein can be applied to good advantage to detect the localization element/sheath state changes of electrode 17 from FIG. 3A to FIG. 3B, and of electrode 52 from FIG. 3B to FIG. 3C (and, as the ordinarily skilled artisan would appreciate, vice versa, as well as for electrodes 54 and 56 should catheter 13 be further advanced from and/or withdrawn into sheath 35).

Returning now to FIG. 1, in some embodiments, a fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the measurement electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20, for example, may comprise a conventional general-purpose computer, a special-purpose computer, a distributed computer, or any other type of computer. The computer 20 may comprise one or more processors 28, such as a single central processing unit (CPU), or a plurality of processing units, commonly referred to as a parallel processing environment, which may execute instructions to practice the various aspects disclosed herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any other number of electrodes) could be positioned in any other effective arrangement for driving a current to or sensing a current from an electrode in the heart. For example, multiple electrodes could be placed on the back, sides, and/or belly of patient 11. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The measurement electrodes 17, 52, 54, 56 placed in the heart 10 are exposed to the field from a current pulse and are measured with respect to ground, such as belly patch 21. In practice the catheters within the heart 10 may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the measurement electrodes 17, 52, 54, 56 within heart 10.

The measured voltages may be used by system 8 to determine the location in three-dimensional space of the electrodes inside the heart, such as measurement electrodes 17, 52, 54, 56, relative to a reference location, such as reference electrode 31. That is, the voltages measured at reference electrode 31 may be used to define the origin of a coordinate system, while the voltages measured at measurement electrodes 17, 52, 54, 56 may be used to express the location of measurement electrodes 17, 52, 54, 56 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

In one representative embodiment, the system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ cardiac mapping and visualization system of St. Jude Medical, Inc., which generates electrical fields as described above, or another such system that relies upon electrical fields. Other systems, however, may be used in connection with the present teachings, including for example, the CARTO navigation and location system of Biosense Webster, Inc., the AURORA® system of Northern Digital Inc., or Sterotaxis' NIOBE® Magnetic Navigation System, all of which utilize magnetic fields rather than electrical fields. The localization and mapping systems described in the following patents (all of which are hereby incorporated by reference in their entireties) can also be used: U.S. Pat. Nos. 6,990,370; 6,978,168; 6,947,785; 6,939,309; 6,728,562; 6,640,119; 5,983,126; and 5,697,377.

Thus, the present invention will be described in the context of a localization system that generates an electrical field. The fields generated by localization system 8 will be referred to generically as "localization fields," while the elements generating the fields, such as surface electrodes 12, 14, 16, 18, 19, and 22 will be generically referred to as "localization field generators." As described above, surface electrodes 12, 14, 16, 18, 19, and 22 may also function as detectors to measure the characteristics of the localization field (e.g., the voltages measured at roving electrodes 17, 52, 54, 56, or a current from roving electrodes 17, 52, 54, 56); thus, electrodes 17, 52, 54, and 56 may also be referred to generically as "localization elements" (or, in the case of an impedance-based localization system, more specifically as "localization electrodes"). Further, the measurements of each localization element can be referred to generically as "localization signals."

As previously described, surface electrodes 12, 14, 16, 18, 19, 22 generate electric fields that are in turn sensed by electrodes 17, 52, 54, and 56 on catheter 13. Signal generator 25 can provide an excitation signal to any pair of surface electrodes in the form of a sinusoidal alternating current at, for example, a frequency of 8 kHz, although the ordinarily skilled artisan will appreciate that a broad range of frequencies can be used without departing from the teachings herein.

To determine the electric field intensity at each catheter electrode, the sensed signals can first be frequency limited by low-pass filter 27, then converted to a digital value by analog to digital converter 26. Synchronous demodulation can then be applied to determine the resulting electric field intensity for each electrode and, in turn, each surface electrode pair. Synchronous demodulation is an established method of determining the intensity of a signal at a particular frequency by multiplying the sensed signal (from analog-to-digital converter 26) with an in-phase copy of the excitation signal from signal generator 25. This in-phase copy is known as the sine reference. Before multiplication, the sine reference can be time delayed to phase align it with the sensed signal. The sensed signal has a natural time delay relative to the sine reference due to the electrical path the sensed signal must traverse from signal generator 25, through surface electrodes, body tissue, catheter electrodes, and sensing electronics. The product of the multiplication is averaged of a time period to provide a value that is proportional to the electric field at each catheter electrode. This is the in-phase component and can be used to calculate the relative location of each catheter electrode within the localization field.

By multiplying the same sensed signal with a signal that is 90 degrees out-of-phase with the sine reference signal (by definition, a cosine reference signal), an out-of-phase component is determined. This out-of-phase component is also known as the quadrature component.

In a properly tuned localization system (i.e., a system where the demodulation delay time is optimized), the in-phase component will dominate over the quadrature component. The quadrature component will ideally be zero, but may have a small measureable value. Moreover, provided the localization elements remain outside the introducer sheath, the quadrature component will be substantially constant within a particular anatomical region. The quadrature component can vary somewhat from region-to-region due to the non-homogenous structure of the cardiac space.

When a localization element is withdrawn into the introducer sheath, however, the quadrature component changes measurably. This is due to the impedance change in the vicinity of the localization element. The impedance change results not only from the constricted space and insulating material construction of the introducer sheath, but also from changes in complex impedance (e.g., a combination of resistance and capacitance).

As the ordinarily skilled artisan will appreciate, changes in capacitance change the delay time of a signal sensed by a localization element. It follows that the demodulation delay time is no longer optimized, leading to position sensitivity in the quadrature component. The same lack of optimization renders the in-phase signal unreliable, leading, for example, to difficulties in rendering an image of catheter 13 within the patient's heart. In one embodiment, when a localization element has been withdrawn into the sheath, it may be desirable to detect this transition to enable the transitioning localization element to be temporarily turned off or otherwise disabled as described further below.

Figure 4:
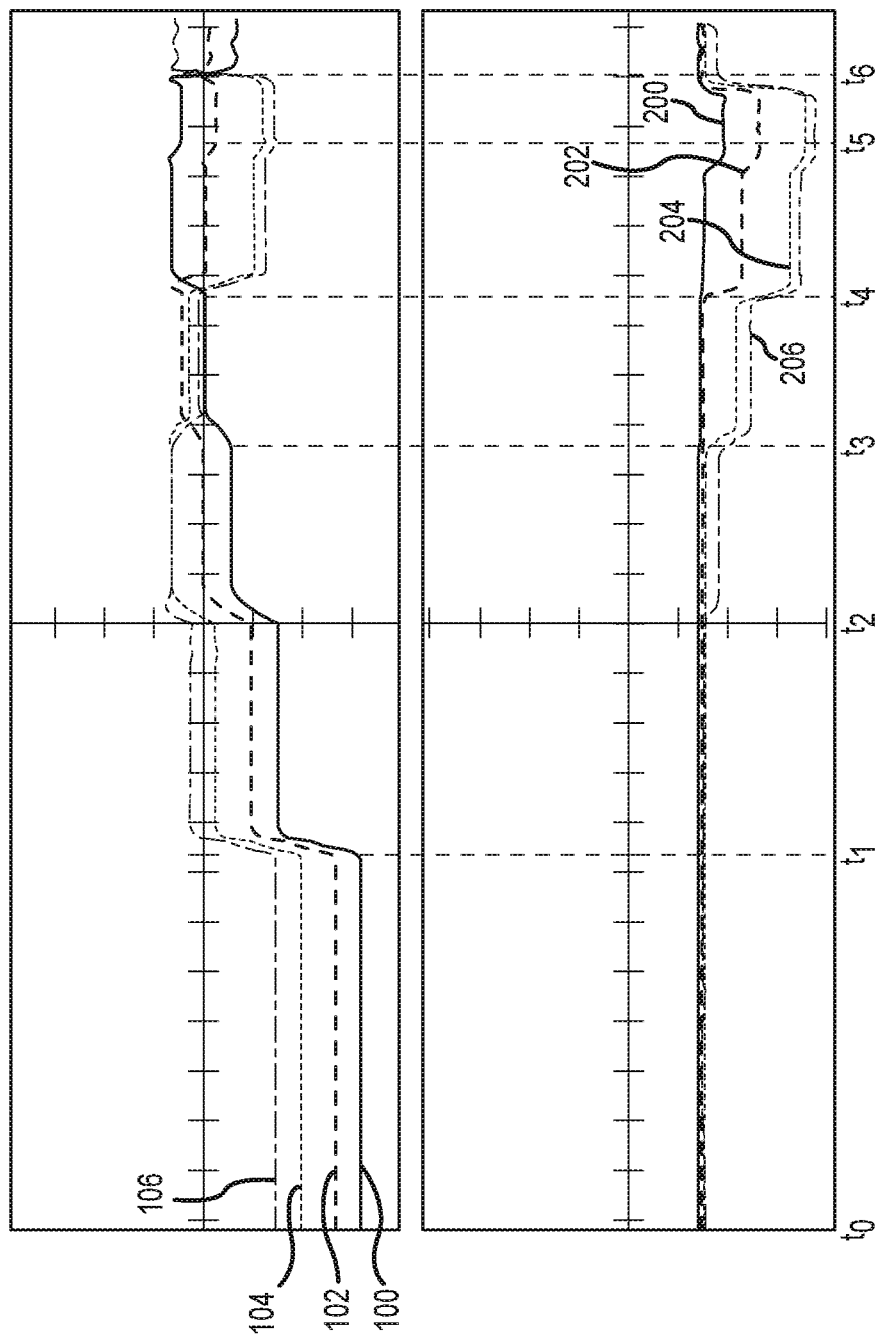
FIG. 4 depicts the in-phase and quadrature components of the localization signals for four localization electrodes.

A method for detecting a localization element/sheath state change based on the quadrature component will now be described with reference to FIGS. 4 and 5. FIG. 4 depicts both the in-phase and quadrature components of the localization signals for four electrodes (e.g., 17, 52, 54, and 56) along the neck-leg axis defined by patch electrodes 18 and 19. The top window of FIG. 4 illustrates the respective in-phase components (100, 102, 104, 106) for these electrodes, while the bottom window illustrates their respective quadrature components (200, 202, 204, 206). At the leftmost edge of FIG. 4 (e.g., time to), all four electrodes 17, 52, 54, 56 are outside of introducer sheath 35. As can be seen in the lower window of FIG. 4, the quadrature component for each of electrodes 17, 52, 54, 56 is non-zero, relatively small, and substantially constant.

At time $t_1$, approximately 4 seconds later, catheter 13 is partially withdrawn into introducer sheath 35. The top window of FIG. 4 shows the displacement change for each electrode, but, because all four electrodes remain outside of introducer sheath 35, the lower window of FIG. 4 shows no change in the quadrature component for any of the electrodes.

At time $t_2$, approximately 2 seconds later, catheter 13 is withdrawn further into introducer sheath 35 to such an extent that most proximal electrode 56 re-enters introducer sheath 35. The top window of FIG. 4 shows the displacement, and further shows an unreliable in-phase component for electrode 56 (line 106). The bottom window of FIG. 4 also shows a measurable change in the quadrature component for electrode 56 (line 206). This measurable change in the quadrature component for electrode 56 is indicative of the localization element/sheath state change for electrode 56.

At time $t_3$, approximately 2 seconds later, catheter 13 is withdrawn further into introducer sheath 35 to such an extent that electrode 54 also re-enters introducer sheath 35. The top window of FIG. 4 shows the displacement, and further shows an unreliable in-phase component for electrode 54 (line 104). The bottom window of FIG. 4 also shows a measurable change in the quadrature component for electrode 54 (line 204), as well as a further change in the quadrature component for electrode 56. This measurable change in the quadrature component for electrode 54 is indicative of the localization element/sheath state change for electrode 54.

At time $t_4$, approximately 1.5 seconds later, catheter 13 is withdrawn further into introducer sheath 35 to such an extent that most distal ring electrode 52 also re-enters introducer sheath 35. The top window of FIG. 4 shows the displacement, and further shows an unreliable in-phase component for electrode 52 (line 102). The bottom window of FIG. 4 also shows a measurable change in the quadrature component for electrode 52 (line 202), as well as further changes in the quadrature components for electrodes 56, 54. This measurable change in the quadrature component for electrode 52 is indicative of the localization element/sheath state change for electrode 52.

At time $t_5$, approximately 1 second later, catheter 13 is withdrawn further into introducer sheath 35 to such an extent that tip electrode 17 also re-enters introducer sheath 35. The top window of FIG. 4 shows the displacement, and further shows an unreliable in-phase component for electrode 17 (line 100). The bottom window of FIG. 4 also shows a measurable change in the quadrature component for electrode 17 (line 200), as well as further changes in the quadrature components for electrodes 56, 54, 52. This measurable change in the quadrature component for electrode 17 is indicative of the localization element/sheath state change for electrode 17.

Finally, at time $t_6$, approximately 1 second later, catheter 13 is advanced back out of introducer sheath 35 such that only the most proximal electrode 56 remains within introducer sheath 35. The top window of FIG. 4 shows the displacement, with the in-phase components for electrodes 17, 52, and 54 (lines 100, 102, 104, respectively) returning to reliable signals. Likewise, the bottom window of FIG. 4 shows that the quadrature components for electrodes 17, 52, and 54 (lines 200, 202, 204, respectively) return to approximate their initial, substantially stable values, indicative of their state change (e.g., re-emergence from introducer sheath 35). Only electrode 56 remains subject to an unreliable in-phase component (line 106) and a measurably changed quadrature component (line 206) because only electrode 56 remains within introducer sheath 35.

Figure 5:
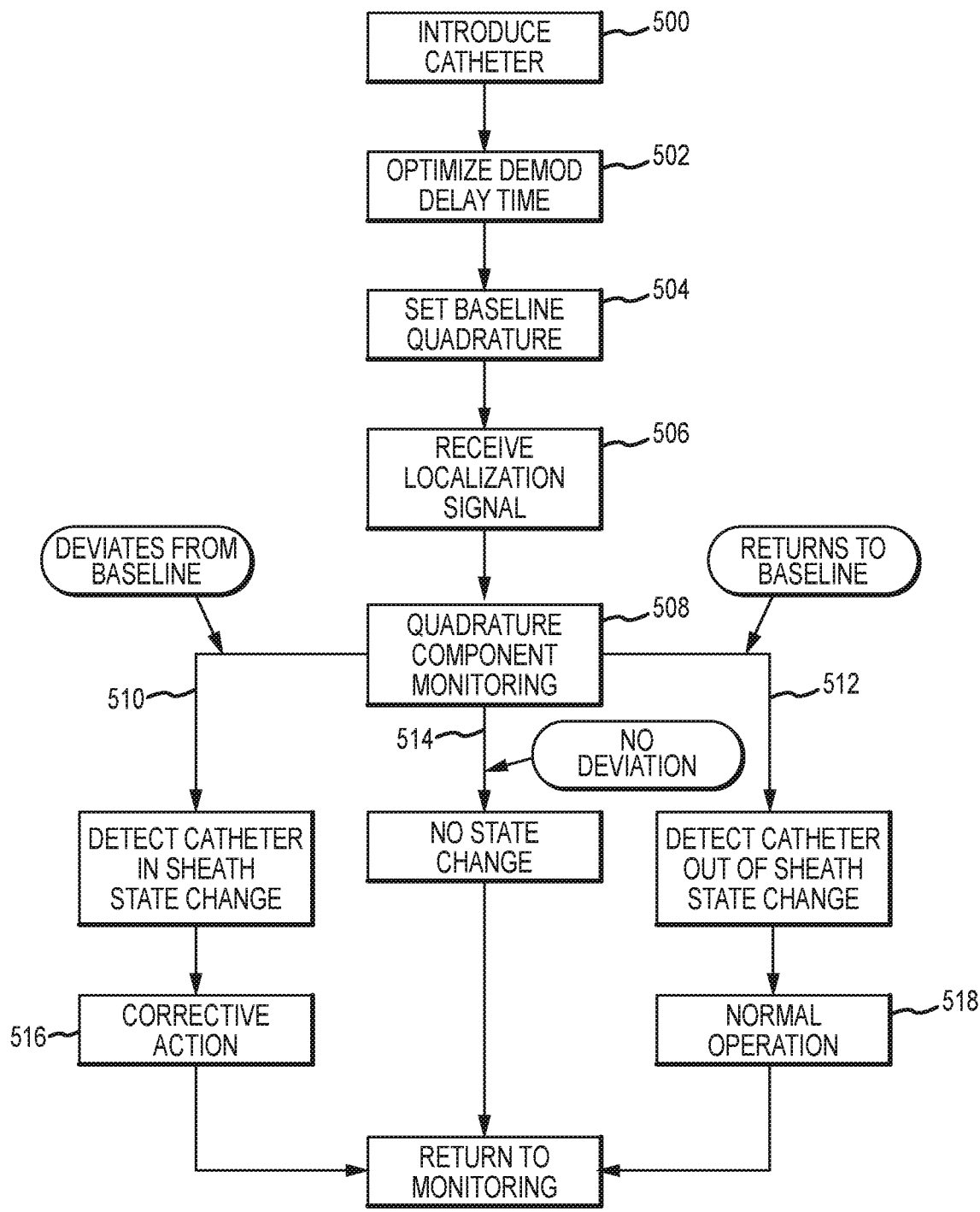
FIG. 5 is a flowchart depicting representative steps of an absolute methodology to detect localization element/sheath state changes according to the teachings herein.

FIG. 5 is a flowchart of representative steps that can be performed in order to detect localization element/sheath state changes. In step 500, catheter 13 is introduced into the localization field generated by localization system 8 (e.g., introduced into the patient's heart). In optional step 502, the delay time of the demodulation signal is optimized. These steps are sufficiently well understood by those of ordinary skill in the art that they need not be further discussed herein.

In step 504, a baseline quadrature component is set, such that localization element/sheath state changes can be detected from the quadrature component of the localization signal for a catheter-borne localization element by comparisons between the real time quadrature component and the baseline quadrature component. The baseline is established with the localization element outside of the introducer sheath (e.g., in the blood pool).

In one embodiment, the baseline quadrature component will follow from the optimization of the demodulation delay time in step 502. Typically, in a properly calibrated (that is, optimized) system, the quadrature component of the localization signal will remain substantially constant at a calibration value as the localization element moves within a particular anatomical region. Localization element movement during calibration can be due to the patient's natural motion (e.g., the beating of the heart). Alternatively, it can be induced, such as by the practitioner making small movements of the catheter. The calibration value for the quadrature component is depicted, for example, in the lower window of FIG. 4 from time $t_0$ to time $t_2$.

As described above, optimization step 502 is optional. Thus, in certain embodiments, the demodulation delay is calculated using a calibration procedure ex vivo. One manner for sufficiently calibrating or "tuning" the localization system involves performing a standard calibration that approximates the delays experienced by the signals in the body, obtaining impedance measurements for both in-phase and out-of-phase with simulated patient impedances, until the out-of-phase signal shows minimal change with simulated location change. As described above, the "location change" can result from normal cardiac rhythm, manual movements of the catheter, and the like. Simulated location changes can be created by invoking small changes in the simulated patient impedance.

Once the baseline quadrature component (e.g., the calibration value) is established, localization element/sheath state changes can be detected from a received localization signal (step 506) by monitoring the quadrature component (step 508) thereof.

For example, the withdrawal of a localization element into the introducer sheath can be detected when the quadrature component for the localization element deviates from the calibration value by more than a preset amount (path 510). This preset amount can be user-adjustable or user-selectable. It can also be a positive and/or negative deviation from the calibration value. For example, in certain aspects, step 504 can include computing the mean and standard deviation of the quadrature component. Then, a localization element/sheath state change can be detected when the quadrature component deviates from the mean by more than a preset number of standard deviations in either direction (e.g., ±3σ).

Conversely, when the quadrature component returns to within a preset amount of the calibration value (path 512), the re-emergence of the localization element from the introducer sheath can be detected.

Similarly, if no change in the quadrature component is detected (path 514), then no localization element/sheath state change is detected.

In response to detecting that a localization element/sheath state change, a number of steps (referred to generally as "corrective actions") can optionally be taken in step 516, either independently or in concert. For example, an alert (e.g., an audible, visual, and/or haptic signal) can be generated to call the practitioner's attention to the withdrawal of a localization element into, or emergence of a localization element from, the introducer sheath.

As another example, data collection can be gated to the in- or out-of-sheath state of a given localization element. That is, when the localization element is within the sheath, data collection therefrom can be suspended; when the localization element is outside of the sheath, data collection therefrom can proceed (step 518).

As still another example, data collected with the localization element within the sheath can simply be discarded.

The foregoing discussion, which detects localization element/sheath state changes by relating the instantaneous quadrature signal(s) to a pre-established baseline can be referred to as "absolute" detection. In another aspect, localization element/sheath state changes can be detected using a "relative" methodology. This relative methodology will be explained with reference to the flowchart of FIG. 6.

Figure 6:
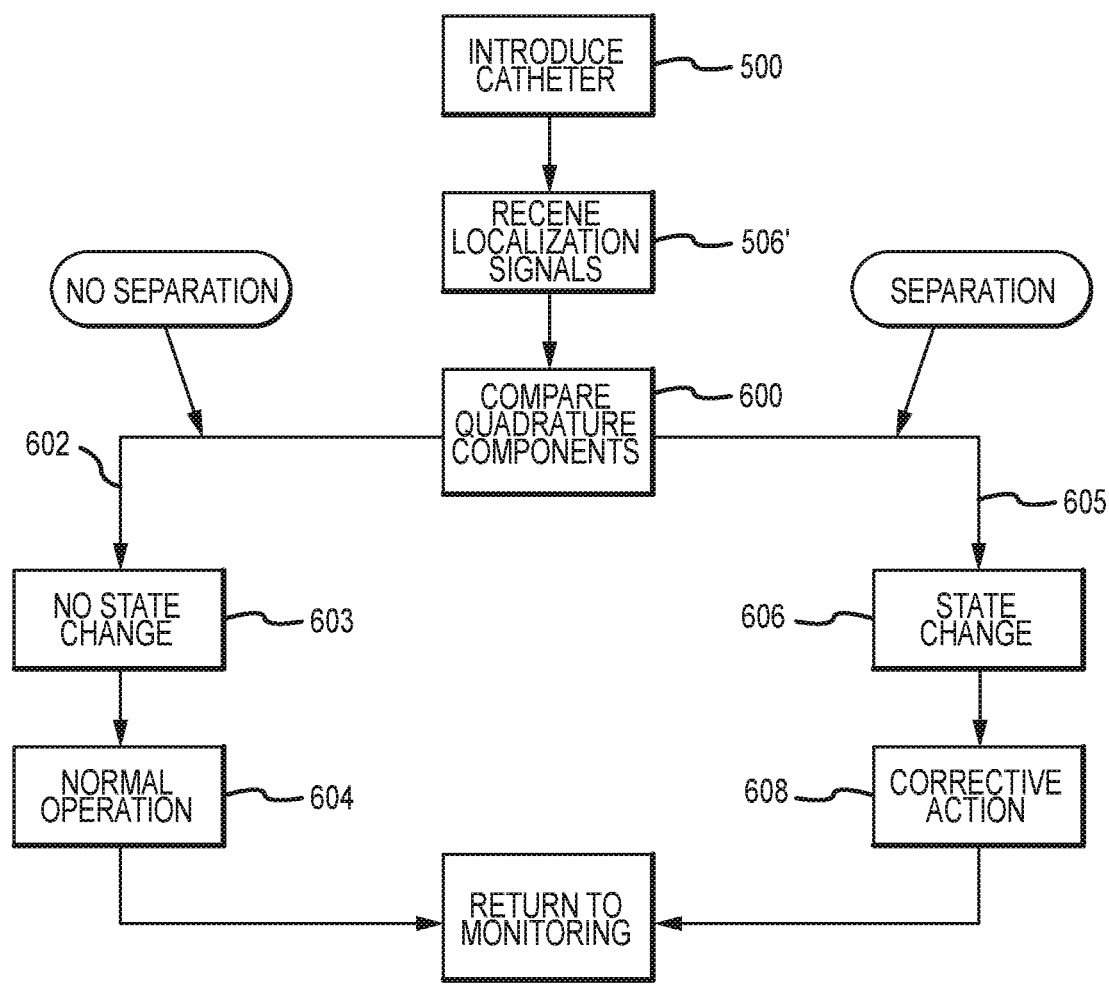
FIG. 6 is a flowchart depicting representative steps of a relative methodology to detect localization element/sheath state changes according to the teachings herein.

Block 500, corresponding to the introduction of catheter 13 into a localization field (e.g., the impedance-based localization field generated by system 8), is the same in FIG. 6. Likewise, localization signals are received in block 506'. In FIG. 6, however, there are at least two localization signals received. For purposes of explanation, this disclosure will assume that these signals are a first localization signal for tip electrode 17 and a second localization signal for ring electrode 52.

As the ordinarily skilled artisan will understand from the foregoing discussion, each signal can be resolved into an in-phase component, which is reflective of the position of the respective electrode within the localization field, and a quadrature component. One of the two quadrature signals (e.g., the first quadrature signal for tip electrode 17) is designated a reference signal for comparison to the other quadrature component in block 600.

A state change between ring electrode 52 and introducer sheath 35 can be detected based on the comparison that takes place in block 600. In particular, it is possible to determine whether ring electrode 52 is within or outside of introducer sheath 35 based on the comparison of the quadrature component of the localization signal for ring electrode 52 to the quadrature component of the localization signal for tip electrode 17.

For example, if there is little or no separation between the quadrature components (path 602), then no state change is detected (block 603), because ring electrode 52 remains outside of introducer sheath 35. Normal operation can continue in block 604.

If, on the other hand, the two quadrature signals separate by more than a preset amount (path 605), then a state change is detected (block 606) because ring electrode 52 has entered introducer sheath 35. If desired, corrective action (e.g., suspending data collection from ring electrode 52 or discarding data collected from ring electrode 52) can take place in block 608.

The ordinarily skilled artisan will appreciate that the teachings above can also be applied to detect re-emergence of ring electrode 52 from introducer sheath 35. For example, when the separation between the two quadrature signals falls below the preset amount (e.g., it returns to a value close to zero), ring electrode 52 can be detected outside introducer sheath 35. In addition, the teachings can also be applied to detect the sheathing and re-emergence of ring electrodes 54 and 56 (or any other electrodes on catheter 13).

Figure 7:
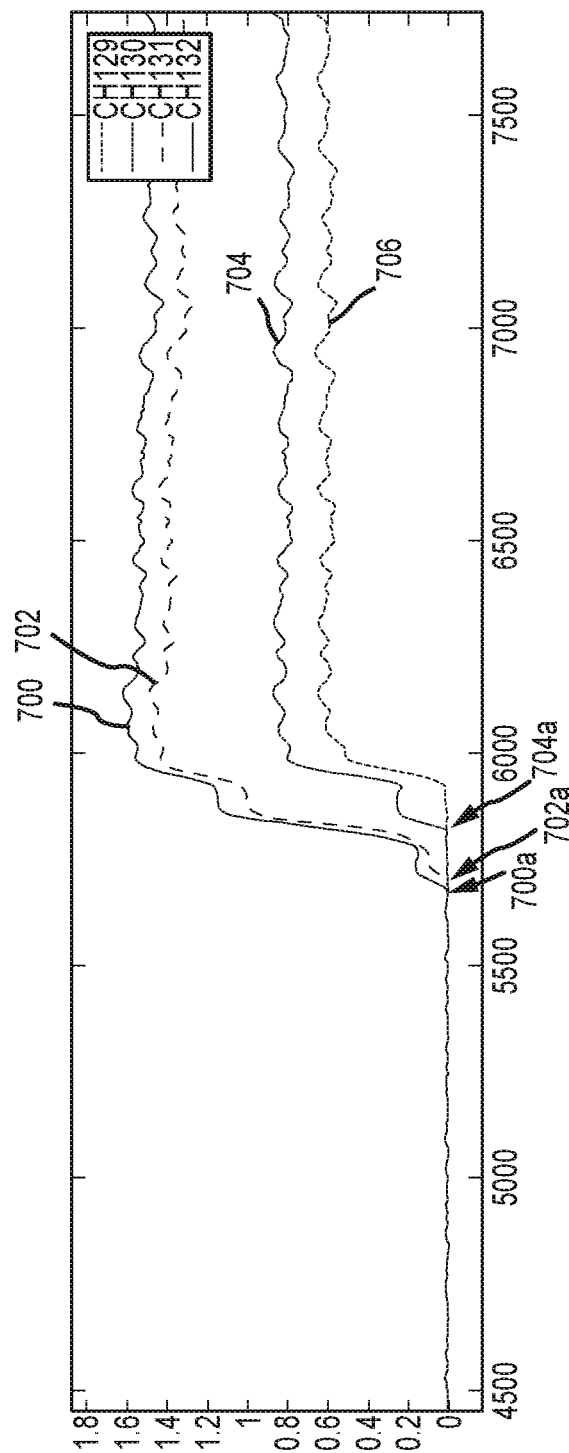
FIG. 7 depicts the quadrature components of the localization signals for four localization electrodes.

FIG. 7 illustrates the relative methodology described above via plots of the quadrature signals for electrodes 56 (trace 700), 54 (trace 702), 52 (trace 704), and 17 (trace 706) over time. The x-axis of FIG. 7 shows samples taken at a frequency of 100 Hz. From about 4400 samples to about 5700 samples (e.g., about 44 seconds to about 57 seconds), all quadrature components are roughly the same, which reflects that all electrodes are outside of introducer sheath 35. At about 5700 samples, however, ring electrode 56 is withdrawn into introducer sheath 35, which results in separation between trace 700 and trace 706 (see arrow 700*a*).

Shortly thereafter, ring electrode 54 is also withdrawn into introducer sheath 35, which results in separation between trace 702 and trace 706 (see arrow 702*a*).

Finally, at about 5900 samples (e.g., about 59 seconds), ring electrode 52 is withdrawn into introducer sheath 35, which results in separation between trace 704 and trace 706 (see arrow 704*a*).

Thus, as shown in FIG. 7, the separation between the quadrature signals can be used to detect localization element/sheath state changes. In some embodiments, only a one-to-one comparison is performed (e.g., the quadrature component for each ring electrode 52, 54, 56 is compared to the quadrature component for tip electrode 17). It is also contemplated, however, that additional comparisons can be made, up to and including a comparison of the quadrature component for each electrode to every other electrode.

If, as described above, the quadrature component for tip electrode 17 is used as the reference for the ring electrodes, the relative methodology cannot be used to detect state changes for tip electrode 17 (because the quadrature component for tip electrode 17 cannot logically be compared to itself). Thus, a different methodology can be used to detect localization element/sheath state changes for tip electrode 17.

As a first order solution, it is clear that, when the distal most ring electrode (i.e., electrode 52) is sheathed, tip electrode 17 is also at risk of becoming sheathed. Thus, an assumption can be made that, whenever ring electrode 52 is detected as sheathed using the relative methodology described above, so too is tip electrode 17 sheathed. (The geometry of catheter 13 also requires that, whenever ring electrode 52 is sheathed, electrodes 54 and 56 are also sheathed, so they can be set to an "in sheath" state whenever ring electrode 52 is detected as sheathed.)

This approach requires at least two electrodes outside of introducer sheath 35 for the electrophysiology study to proceed, a condition that not always be desirable or achievable. In some embodiments, therefore, the absolute methodology described above can be applied to detect localization element/sheath state changes for tip electrode 17 by comparing the quadrature component for tip electrode 17 to a baseline quadrature component. In other words, once ring electrode 52 is detected as sheathed, comparisons between the quadrature component for tip electrode 17 and a baseline quadrature component, established with tip electrode 17 outside introducer sheath 35 as described above, can be initiated to determine when tip electrode 17 withdraws into and/or re-emerges from introducer sheath 35.

In some aspects, the baseline quadrature component for tip electrode 17 is set when ring electrode 52 first withdraws into introducer sheath 35. In other aspects, the baseline quadrature component for tip electrode 17 is computed as a running average of the quadrature component for tip electrode 17 over time. The ordinarily skilled artisan will also recognize that there are other suitable ways to set a baseline quadrature for tip electrode 17.

Moreover, because the quadrature value can vary from region-to-region within the body, it is contemplated to use a plurality of distinct baseline quadrature values, with each corresponding to a particular anatomical region. For example, whenever catheter 13 is moved into a new region with ring electrode 52 unsheathed (which assures that tip electrode 17 is also unsheathed), a baseline quadrature value for tip electrode 17 for that region can be stored. That is, the baseline quadrature value for tip electrode 17 can be associated with one or more positions of catheter 13 within the localization field. Thereafter, whenever catheter 13 is detected in that same region, the corresponding baseline quadrature value can be used to detect state changes for tip electrode 17 (or, if desired, any other electrode on catheter 13).

Although several embodiments of this invention have been described above with a certain degree of particularity, those skilled in the art could make numerous alterations to the disclosed embodiments without departing from the spirit or scope of this invention.

For example, the invention has been described above with reference to the neck-leg axis. The use of the neck-leg axis is desirable because it helps ensure that the quadrature component will be non-zero, because there will be an offset between the location of catheter 13 (e.g., within the heart) and the coordinate reference point for the localization system (e.g., belly patch 21) that will be larger than on other axes. It should be understood, however, that the teachings herein could be applied to any or all measurement axes of localization system 8.

As another example, in another embodiment, the calibration process (502) does not change the demodulation delay time, but rather invokes a linear relationship between the in-phase and quadrature components of localization elements that are not in sheaths. When measuring complex impedance components, any calibration delay offset manifests as a quadrature component that is linearly dependent on the in-phase component. In addition, some constant current may be present in the instrumentation which is out of phase with the localization field generation, resulting in a position-independent quadrature measurement. The plurality of localization elements disposed within the localization field provides a plurality of co-located in-phase and quadrature measurements to which a linear model is fit, such as by using least-squares or another suitable model fitting technique. Alternately, a single localization element may be moved to a plurality of locations in order to acquire a number of co-located in-phase and quadrature measurements to determine the linear model parameters. Once the linear model parameters have been determined, a localization element can be identified as entering the sheath when its in-phase and quadrature measurements no longer fit the parameters, as evidenced by a residual between modeled and measured quadrature values rising above a critical threshold. An ordinarily skilled artisan would be able to extend the described technique to non-linear and multivariate models.

As still another example, the relative methodology is described above with respect to tip electrode 17 as the reference. Any other electrode, or in fact combination of electrodes, on catheter 13 could be used as the reference instead of (or in addition to) tip electrode 17, though more distally-positioned electrodes are advantageous.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electrophysiology system, comprising:
a processor configured to:
receive as input a plurality of localization signals from a respective plurality of localization elements disposed on an electrophysiology catheter;
extract from each localization signal of the plurality of localization signals a respective quadrature component; and
detect whether a first localization element of the plurality of localization elements is positioned within a sheath or positioned outside of the sheath by comparing a first quadrature component of a first localization signal received from the first localization element to a second quadrature component of a second localization signal received from a second localization element.

2. The electrophysiology system according to claim 1, wherein the processor is configured to detect that the first localization element is positioned within the sheath when the comparison between the first quadrature component and the second quadrature component exceeds a preset amount.

3. The electrophysiology system according to claim 2, wherein the processor is further configured to detect that the first localization element has returned to being positioned outside the sheath when the comparison between the first quadrature component and the second quadrature component no longer exceeds the preset amount.

4. The electrophysiology system according to claim 1, wherein the processor is further configured to suspend data collection from the first localization element when the processor detects that the first localization element is positioned within the sheath.

5. The electrophysiology system according to claim 1, wherein the processor is further configured to discard data collected from the first localization element when the processor detects that the first localization element is positioned within the sheath.

6. The electrophysiology system according to claim 1, wherein the processor is further configured to set a state of any localization element disposed on the electrophysiology catheter proximal of the first localization element to within the sheath when the processor detects that the first localization element is positioned within the sheath.

7. An electrophysiology system, comprising:
a processor configured to:
receive as input a first localization signal from a first localization element disposed on an electrophysiology catheter, wherein the first localization signal comprises a first quadrature component;
receive as input a second localization signal from a second localization element disposed on the electrophysiology catheter, wherein the second localization signal comprises a second quadrature component;
compare the first quadrature component and the second quadrature component; and
detect a localization element/sheath state change for at least one of the first localization element and the second localization element based on the comparison between the first quadrature component and the second quadrature component.

8. The electrophysiology system according to claim 7, wherein the processor is configured to detect the localization element/sheath state change by detecting that the comparison between the first quadrature component and the second quadrature component exceeds a preset amount, thereby detecting that the at least one of the first localization element and the second localization element has withdrawn into an introducer sheath.

9. The electrophysiology system according to claim 8, wherein the processor is further configured to detect the localization element/sheath state change by detecting that the comparison between the first quadrature component and the second quadrature component returns to a value below the preset amount, thereby detecting that the at least one of the first localization element and the second localization element has reemerged from the introducer sheath.

10. The electrophysiology system according to claim 8, wherein the processor is further configured to set a state of any localization element disposed on the electrophysiology catheter proximal of the at least one of the first localization element and the second localization element to within the sheath upon detecting that the at least one of the first localization element and the second localization element has withdrawn into an introducer sheath.

11. A non-transitory computer readable medium having embodied thereon computer-readable code that, when executed, causes an electrophysiology system to execute steps comprising:
obtaining a first localization signal from a first localization element disposed on an electrophysiology catheter, the first localization signal including a first quadrature component;
obtaining a second localization signal from a second localization element disposed on the electrophysiology catheter, the second localization signal including a second quadrature component;
comparing the first quadrature component to the second quadrature component; and
detecting a localization element/sheath state change for at least one of the first localization element and the second localization element based upon the comparison of the first quadrature component to the second quadrature component.

12. The non-transitory computer readable medium according to claim 11, wherein detecting a localization element/sheath state change for at least one of the first localization element and the second localization element comprises detecting withdrawal of one of the first localization element and the second localization element into an introducer sheath when the comparison of the first quadrature component to the second quadrature component exceeds a preset amount.

13. The non-transitory computer readable medium according to claim 12, wherein detecting a localization element/sheath state change for at least one of the first localization element and the second localization element further comprises detecting reemergence of the one of the first localization element and the second localization element from the introducer sheath when the comparison of the first quadrature component to the second quadrature component returns to a value below the preset amount.

* * * * *